United States Patent [19]

Lampe et al.

[11] Patent Number: 5,251,470
[45] Date of Patent: Oct. 12, 1993

[54] HOUSING FOR FAST EXHAUST GAS SENSORS FOR A CYLINDER-SELECTIVE LAMBDA MEASUREMENT IN AN INTERNAL COMBUSTION ENGINE

[75] Inventors: Uwe Lampe, Erding; Wolfgang Hanrieder, Munich; Hans Meixner, Haar, all of Fed. Rep. of Germany

[73] Assignee: Siemens Aktiengesellschaft, Munich, Fed. Rep. of Germany

[21] Appl. No.: 832,801

[22] Filed: Feb. 7, 1992

[30] Foreign Application Priority Data

Mar. 21, 1991 [DE] Fed. Rep. of Germany ....... 4107908

[51] Int. Cl.$^5$ ........................................... G01N 27/416
[52] U.S. Cl. .................................... 73/31.05; 55/455; 204/428
[58] Field of Search ............... 73/23.31, 31.07, 863.21, 73/863.22, 863.23, 863.41, 863.51, 23.32, 31.05; 55/307, 434, 442, 447, 455, 459.1, 385.3, 462, 465; 204/428

[56] References Cited

U.S. PATENT DOCUMENTS

| | | | |
|---|---|---|---|
| 1,753,972 | 4/1930 | Schutz | 55/455 |
| 4,038,034 | 7/1977 | Nakajima et al. | 204/428 X |
| 4,309,897 | 1/1982 | Springer et al. | 73/23.31 |
| 4,578,174 | 3/1986 | Kato et al. | 204/428 X |
| 4,916,934 | 4/1990 | Nagata et al. | 204/428 X |

OTHER PUBLICATIONS

Zapfe, Carl A. "Stainless Steel" in: McGraw-Hill Encyclopedia of Science and Technology (1977 ed.) vol. 13, pp. 33.

Primary Examiner—Hezron E. Williams
Assistant Examiner—Michael Brock
Attorney, Agent, or Firm—Hill, Steadman & Simpson

[57] ABSTRACT

A housing for a fast exhaust gas sensor for cylinder-selective lambda measurements in an internal combustion engine comprises a hollow-cylindrical housing having at least two slot shaped openings that are arranged rotationally symmetrical over the circumference of the wall of the housing and extend parallel to the axis of the housing. Each of the slot shaped openings have edges that are overlapping in the fashion of a venetian blind so that the rotational symmetrical arrangement of the openings allows the housing and the exhaust gas sensor mounted within the housing to be integrated in an arbitrary rotational attitude relative to the exhaust gas stream in a pipe of a system.

6 Claims, 1 Drawing Sheet

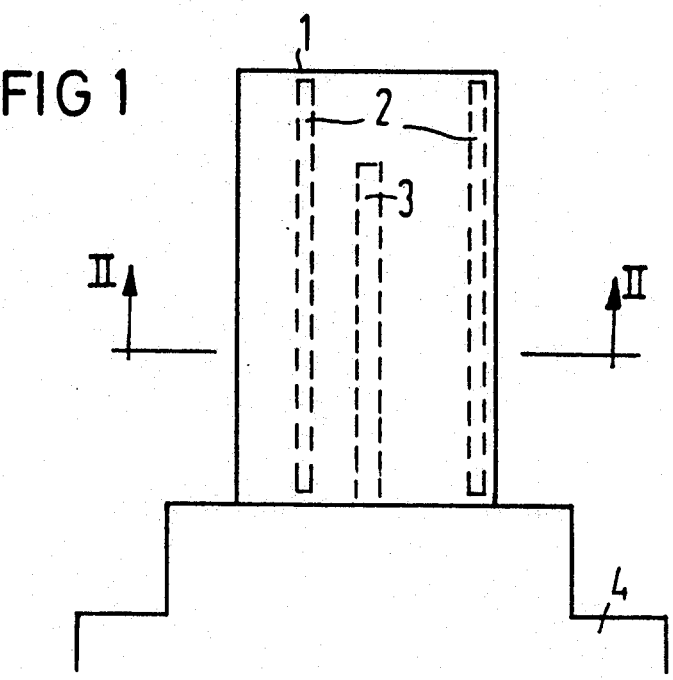
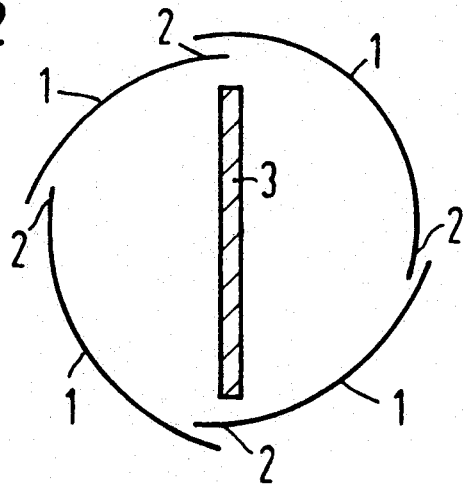

HOUSING FOR FAST EXHAUST GAS SENSORS FOR A CYLINDER-SELECTIVE LAMBDA MEASUREMENT IN AN INTERNAL COMBUSTION ENGINE

BACKGROUND OF THE INVENTION

The present invention is directed to a housing for a fast exhaust sensor for a cylinder-selective lambda measurement in an internal combustion engine. The housing has a hollow cylindrical form and has at least two slot shaped openings which are arranged rotational symmetrical over its circumference and lie parallel to the axis of the hollow cylindrical housing with the edges overlapping in a fashion of a venetian blind.

What is referred to as a fast exhaust gas sensor shall be advantageously utilized in the future for cylinder-selective lambda control. A sensor effect of these fast exhaust gas sensors is based on the gas sensitivity of the electrical conductivity of certain semiconductor metal oxides. Up to now, the lambda control occurs with what was referred to as a slow sensors that are only in the position to adequately detect stationary operation. It will be possible to also control the non stationary operating conditions of an internal combustion engine with the anticipated, new probes. The preferred gas sensitive materials are either strontium titanate or cerium oxide. In order to achieve an adequate high response speed, these gas sensitive metal oxides are to be applied to the substrate of the sensor as either a thin film or as a thick film.

As known, the exhaust gas of internal combustion engines is loaded with particles. These particles occur from the additives and from the impurities of the fuel supplies such as lubricating oil, benzene, etc. and due to abrasion of motor parts. The particles have a typical size of 1 through 2 micrometers and are composed among other things, of iron oxide. The deposited particle layer has a considerable electrical conductivity. Solid deposits will short circuit the sensor layer given either the thick film or thin film sensors. Even a slight deposit of these particles on the gas sensitive element of the sensor changes the gas-sensitive and electrical properties thereof and will lead to a degradation so that the desired useful life of the sensor cannot be achieved.

Exhaust gas sensors having a gas-sensitive thin films are previously unknown. The known electrochemical or resistive exhaust gas sensors are executed as a bulk ceramic or as thick film sensors. They are considerably less sensitive to contamination due to the particles but do not achieve the high response speeds required for a cylinder-selective lambda measurement. In order to prevent solid deposits, the "viewing openings" of the sensor are kept as small as possible and the sensor is coated with an inert, porous protective layer. Since slight deposits do not deteriorate the sensor function, no particular value is attached to an optimum flow-through of the housing and to keeping the particles entirely away in the known solutions.

SUMMARY OF THE INVENTION

The object of the present invention is to create a housing for fast exhaust gas sensors which are based on the gas sensitivity of the electrical conductivity of a semiconductor metal oxides with which a circuit flow-over of the sensor by the exhaust gas is presented as a result whereof the depositing of particles is prevented and wherein the gas exchange is not impeded so that the response speed of the sensor is not diminished.

In order to achieve these objects, the invention is directed to a housing for a fast exhaust gas sensor for a cylinder-selective lambda measurements in an internal combustion engine, said housing being a hollow-cylindrical housing and comprising at least two slot shaped openings arranged rotationally symmetrically over the circumference of the housing and extending parallel to the axis of the hollow-cylindrical housing, the edges of said openings overlapping in the fashion of a venetian blind.

Additional features of the invention are utilizing three, four or five slot shaped openings, that the housing is formed of a heat-resistant, and corrosion-free material for example, stainless steel. Other advantages and features of the invention will be readily apparent from the following description of the preferred embodiments, the drawings and claims.

BRIEF DESCRIPTION OF THE DRAWINGS

FIG. 1 is a side view of a sensor housing in accordance with the present invention;

FIG. 2 is a cross-sectional view taken along lines II—II of FIG. 1.

DESCRIPTION OF THE PREFERRED EMBODIMENTS

The principles of the present invention are particularly useful when incorporated in a housing 1 for a sensor as illustrated in FIGS. 1 and 2. The housing 1 has a multitude of openings 2 which serve as openings that act as particle traps and prevent a deposit of particles from an exhaust gas and also allow a fast gas exchange so that the response speed is not diminished. In the preferred embodiment, of the invention illustrated in FIG. 1, four narrow slots 2 are provided in preferably a rotationally symmetrical around the axis of the cylindrical housing 1. A venetian-blind-like overlap of the respective edges of the wall at each of the slots is achieved for example by a suitable bending of the housing wall. This structure has the following advantages:

a direct flow-over of the sensor by the exhaust gas is prevented and as a result thereof the deposit of particles can be prevented;

The gas exchange is not impeded so that the response speed of the sensors is not diminished; and The sensor is rotationally-symmetrical and can be placed in an arbitrary attitude relative to the exhaust gas system.

As illustrated in FIG. 2, the sensor housing 1 of FIG. 1 with its slot-shaped openings 2 has the wall of the housing overlapped in a fashion of a venetian blind. An exhaust gas sensor 3 is arranged and mounted in a known way inside of the sensor housing. The sensor housing is applied in the standard way to a base 4 (FIG. 1) that preferably includes screw threads for being threaded into an exhaust pipe or the like.

Instead of having four slot-shaped openings 2 as illustrated, the housing can be provided with only three slot-shaped openings or with five openings.

The housing is composed of a heat-resistant, corrosion-free material. Preferably this material is stainless steel, for example, a V4A.

Although various minor modifications may be suggested by those versed in the art, it should be understood that we wish to embody within the scope of the patent granted hereon all such modifications as reasonably and properly come within the scope of our contribution to the art.

We claim:

1. In a housing for a fast exhaust sensor for a cylinder-selective lambda measurement in an internal combustion engine, said housing being a hollow-cylindrical housing for receiving the sensor, and having at least one opening for enabling exhaust gas to enter the housing for sensing, the improvements comprising means for preventing deposit of particles on the sensor, said means for preventing consisting of at least two slot-shaped openings arranged rotationally symmetrically in the circumferential wall of the cylindrical housing and extending parallel to an axis of the cylindrical housing, each of the openings having one long edge which overlaps the other long edge in the fashion of a venetian blind.

2. In a housing according to claim 1, wherein the housing has four slot-shaped openings.

3. In a housing according to claim 1, wherein the housing is formed of a material of a heat-resistant and corrosion-resistant material.

4. In a housing according to claim 3, wherein said material is stainless steel.

5. In a housing according to claim 4, wherein the housing has four slot-shaped openings.

6. In a housing according to claim 3, wherein the housing has four slot-shaped openings.

* * * * *